United States Patent [19]

Härtner

[11] Patent Number: 4,532,369
[45] Date of Patent: Jul. 30, 1985

[54] PROCESS FOR THE PREPARATION OF [2,2]-PARACYCLOPHANE

[75] Inventor: Hartmut Härtner, Mühltal, Fed. Rep. of Germany

[73] Assignee: Merck Patent Gesellschaft mit beschränkter Haftung, Darmstadt, Fed. Rep. of Germany

[21] Appl. No.: 546,353

[22] Filed: Oct. 28, 1983

[30] Foreign Application Priority Data

Oct. 30, 1982 [DE] Fed. Rep. of Germany ....... 3240303

[51] Int. Cl.$^3$ .......................... C07C 2/72; C07C 1/00
[52] U.S. Cl. ..................................... 585/428; 585/469
[58] Field of Search ............................... 585/469, 428

[56] References Cited

U.S. PATENT DOCUMENTS

| 3,247,274 | 4/1966 | Pollart | 585/428 |
| 3,258,504 | 6/1966 | Lenaers et al. | 585/428 |
| 3,271,470 | 9/1966 | Spence et al. | 585/428 |
| 3,271,471 | 9/1966 | Baker et al. | 585/428 |
| 3,412,167 | 11/1968 | Lewis | 585/428 |

OTHER PUBLICATIONS

H. E. Winberg, F. S. Fawcett, W. E. Michel and C. W. Theobald, J. Am. Chem. Soc., 82, 1428 (1960).
Chem. Abstracts, 15353(a), 1960.
Yoshihiko Ito, Satoru Miyata, Masashi Natsuka, Takeo Saegusa, J. of Organic Chemistry, 46, 1043–1044 (1981).
L. A. Enede, R. S. Gregorian and John M. Hayt, J. of Am. Chem. Soc., 82, 5218 (1960).

Primary Examiner—D. E. Gantz
Assistant Examiner—Cynthia A. Prezlock
Attorney, Agent, or Firm—Millen & White

[57] ABSTRACT

A process for the preparation of [2,2]-paracyclophane comprises contacting aqueous p-methylbenzyltrimethylammonium hydroxide with sodium hydroxide or potassium hydroxide, in the presence of dimethyl sulfoxide, and preferably in the further presence of an inert water-immiscible organic solvent.

9 Claims, No Drawings

PROCESS FOR THE PREPARATION OF [2,2]-PARACYCLOPHANE

BACKGROUND OF THE INVENTION

The invention relates to a new and improved process for the preparation of [2,2]-paracyclophane (I).

I is a known substance which can be used as an intermediate, inter alia, for the preparation of poly-p-xylylene, which is useful for coating electronic components and assemblies and other precision parts.

Several processes have been described for the preparation of I, but these have considerable disadvantages for industrial production.

Thus, Hofmann elimination, from p-methylbenzyltrimethylammonium hydroxide (II) in the presence of a base (compare Organic Syntheses, Coll. Vol. 5, John Wiley & Sons, Inc., New York/London/Sydney/Toronto, 1973, pages 883–886; Thesis R. Näder, Univ. Göttingen, 1978, page 89) and pyrolysis of p-xylene with water vapor at about 900° C., each give only low yields (maxima of 17–19% reported); in addition, undesired polymeric products are produced to a greater or lesser extent (up to 80%).

In the 1,6-elimination of (p-trimethylsilylmethylbenzyl)trimethylammonium iodide with tetrabutylammonium fluoride (compare J. Org. Chem., Volume 46, 1981, pages 1043–1044) the yield is in fact higher (56%), but the starting materials are not readily accessible and are costly, so that this process is not suitable for industrial preparation.

OBJECTS OF THE INVENTION

One object of the invention is to provide an improved process for the preparation of I, which process either does not have the disadvantages of the known processes or has them to a lesser extent and, in particular, which leads to higher yields.

Upon further study of the specification and appended claims, further objects and advantages of this invention will become apparent to those skilled in the art.

SUMMARY OF THE INVENTION

These objects can be attained by a process for preparing [2,2]-paracyclophane, comprising the steps of contacting aqueous p-methylbenzyltrimethylammonium hydroxide with sodium hydroxide or potassium hydroxide, in the presence of dimethyl sulfoxide.

DETAILED DISCUSSION

It has now been found that the yield in the Hofmann elimination can be increased to 70% when the base used is NaOH or KOH and the process is carried out in the presence of dimethyl sulfoxide (DMSO).

This result was surprising because the addition of other comparable aprotic solvents, such as dimethylformamide, N-methylpyrrolidone or sulfolane, has no effect.

It is particularly advantageous to use concentrated aqueous sodium hydroxide solution or aqueous potassium hydroxide solution and an additional inert water-immiscible organic solvent. Particularly suitable solvents are hydrocarbons, preferably toluene or xylene, but also benzene or tetralin. In such cases, the reaction mixture contains an aqueous phase and an organic phase, which is particularly advantageous.

The reaction temperatures are preferably between about 50° and 130° C., particularly preferably between 75° and 95° C. It is advantageous to agitate the reaction mixture, generally for several hours to several days, until the reaction is substantially complete.

The starting material II is preferably formed in situ by the action of a base on an appropriate quaternary salt, preferably p-methylbenzyltrimethylammonium chloride (III) or bromide.

Advantageously, the ammount of DMSO used is 1–5 volume parts per volume part of aqueous NaOH or KOH solution. If an inert, water-immiscible organic solvent is used, it is preferable present in an amount of 5–50 volume parts per volume part of aqueous NaOH or KOH solution.

The amount of base used will generally be 1–10 moles of base per mole of III or the corresponding bromide.

A particularly preferred procedure comprises adding toluene and DMSO to approximately 45–50% sodium hydroxide or potassium hydroxide solution and then adding dropwise with stirring, at about 75°–95° C., a concentrated aqueous solution of the salt (for example III) and continuing to stir while heating to maintain the temperature for about 10–100 hours. Under these conditions, the workup is particularly simple, and involves merely separating the aqueous and organic phases, washing and drying the organic phase, concentrating the toluene solution, and recovering the resultant solid product, which can be further purified by conventional means, e.g., recrystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

3 liters of toluene and 600 ml of DMSO are added to a solution of 210 g (5.25 moles) of NaOH in 240 ml of water, and then a solution of 150 g (0.75 mole) of III in 90 ml of water is added dropwise, with stirring at 90° C., over the course of 1 hour. II is formed as an intermediate but is not isolated. Stirring is continued for 40 hours at 90° C., the phases are separated, the organic phase is washed with water, filtered, the solution is concentrated and 55 g of [2,2]-paracyclophane, m.p. 275°, are obtained. Yield: 70%.

EXAMPLE 2

The process of Example 1 is repeated, except that 294 g (5.16 moles) of KOH are used in place of NaOH, and the result obtained is comparable.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for preparing [2,2]-paracyclophane, comprising the step of contacting aqueous p-methylbenzyltrimethylammonium hydroxide with sodium hydroxide or potassium hydroxide, in the presence of dimethyl sulfoxide.

2. The process of claim 1, wherein the p-methylbenzyltrimethylammonium hydroxide is generated in situ by contacting aqueous p-methylbenzyltrimethylammonium chloride or bromide with a base.

3. The process of claim 1, wherein said contacting is effected in the further presence of an inert water-immiscible hydrocarbon solvent.

4. The process of claim 3, wherein said inert solvent is benzene, toluene, xylene or tetralin.

5. The process of claim 1, wherein said contacting is effected at a temperature of 50°–130° C.

6. The process of claim 5, wherein said temperature is 75°–95° C.

7. The process of claim 1, wherein a concentrated aqueous solution of p-methylbenzyltrimethylammonium chloride is added portionwise, with stirring, to a mixture of 1 volume part 45–50% aqueous sodium hydroxide or potassium hydroxide, 5–50 volume parts toluene and 1–5 volume parts dimethyl sulfoxide, said mixture containing at least a stoichiometric amount of base, at a temperature of 75°–95° C.; stirring and heating at 75°–95° C. is continued for about 10–100 hours; and resultant [2,2]-paracyclophane is recovered from the organic phase.

8. In a process for preparing [2,2]-paracyclophane by Hofmann elimination, wherein p-methylbenzyltrimethylammonium hydroxide is heated and resultant [2,2]-paracyclophane is recovered, the improvement wherein the reaction is effected by heating aqueous p-methylbenzyltrimethylammonium hydroxide, in contact with an inert water-immiscible organic solvent, and in the presence of dimethyl sulfoxide.

9. The process of claim 8, wherein the p-methylbenzyltrimethylammonium hydroxide is generated in situ by contacting aqueous p-methylbenzyltrimethylammonium chloride or bromide with sodium or potassium hydroxide.

* * * * *